United States Patent [19]
Zanger et al.

[11] Patent Number: 5,392,653
[45] Date of Patent: Feb. 28, 1995

[54] PRESSURE TRANSDUCER MAGNETICALLY-COUPLED INTERFACE COMPLEMENTING MINIMAL DIAPHRAGM MOVEMENT DURING OPERATION

[75] Inventors: Frank Zanger, Hayward; Tim Surber, San Leandro; Donald E. Lehmer, Berkeley, all of Calif.

[73] Assignee: Allergan, Inc., Irvine, Calif.

[21] Appl. No.: 168,870

[22] Filed: Dec. 16, 1993

Related U.S. Application Data

[63] Continuation-in-part of Ser. No. 893,331, Jun. 3, 1992, abandoned.

[51] Int. Cl.6 .............................. G01L 7/00; G01L 9/04
[52] U.S. Cl. ........................................ 73/756; 73/726; 128/675
[58] Field of Search ................. 73/730, 723, 724, 725, 73/726, 727, 728, 754, 756; 128/675; 338/4

[56] References Cited

U.S. PATENT DOCUMENTS

| | | | |
|---|---|---|---|
| 2,535,998 | 12/1950 | Bierman | 338/4 X |
| 3,738,356 | 6/1973 | Workman | 73/701 X |
| 4,227,420 | 10/1980 | Lamadrid | 73/756 |

*Primary Examiner*—Herbert Goldstein
*Assistant Examiner*—Joseph L. Felber
*Attorney, Agent, or Firm*—Walter A. Hackler

[57] ABSTRACT

A pressure measurement system includes a diaphragm and a chamber for exposing one side of the diaphragm to a fluid. A force transducer is provided for measuring force exerted by the fluid on the one side of the diaphragm independent of diaphragm position. A ferromagnetic plate is attached to the diaphragm to enable removable coupling of the diaphragm with a magnet permanently attached to the force transducer.

15 Claims, 3 Drawing Sheets

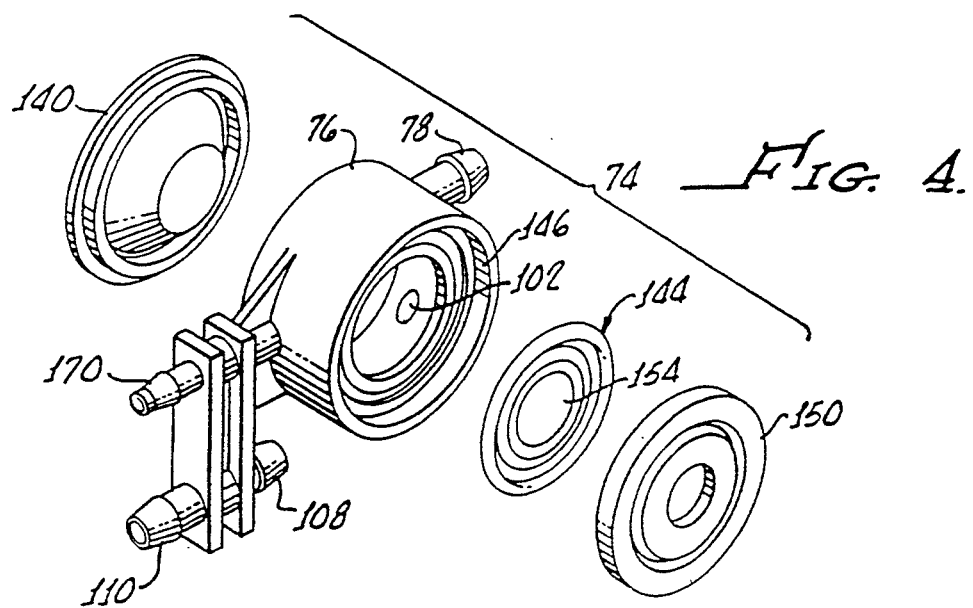
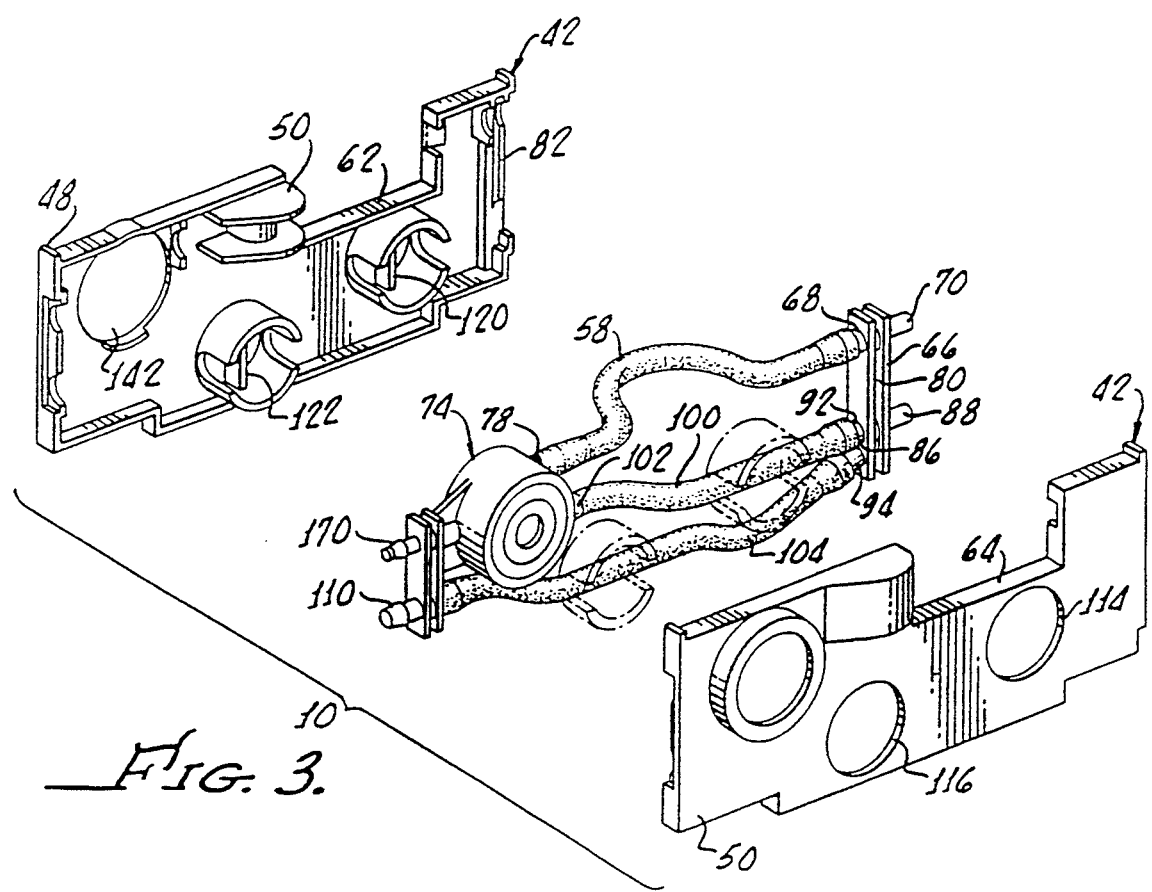

PRESSURE TRANSDUCER MAGNETICALLY-COUPLED INTERFACE COMPLEMENTING MINIMAL DIAPHRAGM MOVEMENT DURING OPERATION

This application is a continuation-in-part of U.S. Ser. No. 07/893,331, filed Jun. 3, 1992, now abandoned.

FIELD OF THE INVENTION

The present invention generally relates to a pressure measurement system and more particularly is related to a pressure monitoring system for ophthalmic instruments such as a Phaco instrument for removing the crystalline lens from an eye.

Typically, cataracts, or crystalline manifestations, in an eye are removed by fragmentation thereof which may include an ultra-sound driven hollow needle inserted into the eye through a small incision in the sclera. Removal of the fragmented lens is effected through a center hole in the needle and involves continuous circulation of fluid through the eye which is provided by the hollow needle inserted therein.

While eye pressure must be carefully maintained to prevent collapse of the eye chamber, over-pressure may be necessary at times to remove a blockage in the hollow needle which may be caused by a fragmented lens. In addition, fluid flow in the needle may be reversed to reflux the fluid and dislodge the fragmented lens from the hollow needle. During this operation, it is, of course, necessary to monitor and maintain eye pressure preselected absolute maximum level.

Failure to measure and control fluid pressure during the removal process may result in the formation of a large void in the plastic tubing system leading from the needle to a pump utilized in providing the fluid circulation. In addition, a sudden release of blockage could result in the reduction of pressure in the eye as the void is filled by the liquid from the eye which may not be replaced with sufficient speed, thereby resulting in the collapse of the cornea as hereinabove pointed out.

Conversely, if there is poor control during the reflux process, a large over-pressure may be generated in the eye which would cause inflation of the eye when the blockage breaks free.

A number of peristaltic pumps have been developed for use with Phaco instruments such as described in U.S. Pat. No. 5,230,614, entitled "Reduced Pulsation Tapered Ramp Pump Head," assigned to the assignee of the present application. This above-referenced patent is incorporated herein by specific reference thereto.

Heretofore, pressure measurement systems, utilizing a diaphragm for the isolated measurement of pneumatic or hydraulic pressure, have incorporated the diaphragm in a number of different structural configurations.

First, the diaphragm has been attached to known spring systems in order to determine the motion of the diaphragm in response to pneumatic and/or hydraulic pressure. This is a traditional method of measuring pressure and is commonly used in many mechanical gauges and pressure transducers. However, since unlimited diaphragm motion is not possible, saturation may occur. This condition effectively puts a maximum pressure measurement limitation on the system. Further, this system requires accurate position measurements and diaphragm characteristics also affect the linear performance of the measurement system.

Other prior art systems have utilized a second, closed pneumatic or hydraulic system on an opposite side of the diaphragm and apparatus for measuring the pressure in the second system caused by motion of the diaphragm in response to a primary fluid.

In this system, the secondary fluid in the closed pneumatic system eliminates the position requirement on the diaphragm necessitated by the spring system, but is still subject to saturation. However, it also adds a requirement of an absolutely no-leak system, since any volume lost on the nonsterile side of the diaphragm, after the diaphragm is first attached, is lost.

This loss of volume makes saturation more likely, and if there is also the possibility of compressing the volume on the nonsterile side of the diaphragm as it is installed, creating a pressure offset.

A similar prior art system utilizes a second, closed pneumatic system on the nonsterile side of the diaphragm. However, in this system, pressure is generated in the second closed system to maintain a constant position of the diaphragm. Measurement of the pressure in this second system is a measurement of the pressure on the sterile side of the diaphragm.

It should be obvious that this last-mentioned system eliminates the need for a no-leak system and the possibility of saturation. However, it reintroduces the position measurement requirement and, in addition, adds the requirement of a controllable pressure source. This secondary pressure source and controlled system also can induce the possibility of servo oscillation.

The apparatus in accordance with the present invention enables the measurement of pressure through the use of force measurement devices without the necessity of position measurement systems. In addition, precise measurement of the diaphragm position is not required.

It is also necessary that the system be sterile and either disposable or autoclavable and further, the system must operate to transmit the pressure data while keeping the liquid system sterile.

SUMMARY OF THE INVENTION

A pressure measurement system in accordance with the present invention generally includes a diaphragm and means for exposing one side of the diaphragm to a fluid. A force transducer provides means for measuring force exerted by the fluid on the one side of the diaphragm without significant movement of diaphragm position. This force measurement eliminates a number of practical problems associated with the changing characteristics of the diaphragm as a function of its position. That is, the actual diaphragm displacement is not, in fact, measured; rather, the force exerted on the diaphragm is directly measured which relates to a true measure of the pneumatic or hydraulic pressure exerted on the other side of the diaphragm.

Naturally, since displacement is not measured, the need for a calibrated spring, for example, to relate force displacement is not required.

Importantly, means are also provided in accordance with the present invention for removably coupling the force transducer means to an opposite side of the diaphragm. This feature enables the measurement portion of the system to be removed from the diaphragm which may thereafter be sterilized by autoclaving or, if it is a disposable system, replaced by a new, sterile diaphragm.

More particularly, a chamber for disposing the one side of the diaphragm to remove it may include a fluid inlet and a fluid outlet, and the diaphragm may be sealably disposed across an opening in the chamber. A ferromagnetic plate attached to the diaphragm and a magnet attached to the force transducer means provide means for removably coupling the force transducer means to an opposite side of the diaphragm.

The magnet may be a permanent magnet or an electromagnetic device, and means may be provided for detecting positive magnetic coupling between the magnet and the plate. While unnecessary to the operation of the present invention, this device acts as a security system for ensuring that signals from the force transducer are, in fact, caused by pressure exerted in the diaphragm.

With specific reference to the chamber, it may include a cylindrical shape with the opening sealed by the diaphragm being disposed in a flat end of the chamber. In this configuration, the fluid inlet and outlet means are disposed in curved portions of the chamber.

BRIEF DESCRIPTION OF THE DRAWINGS

The advantages and features of the present invention will be better understood by the following description when considered in conjunction with the accompanying drawings in which:

FIG. 3 is an exploded perspective view of the tubing management system in accordance with the present invention;

FIG. 4 is an exploded perspective view of the pressure measurement system;

DETAILED DESCRIPTION OF THE DRAWINGS

Figure 1:
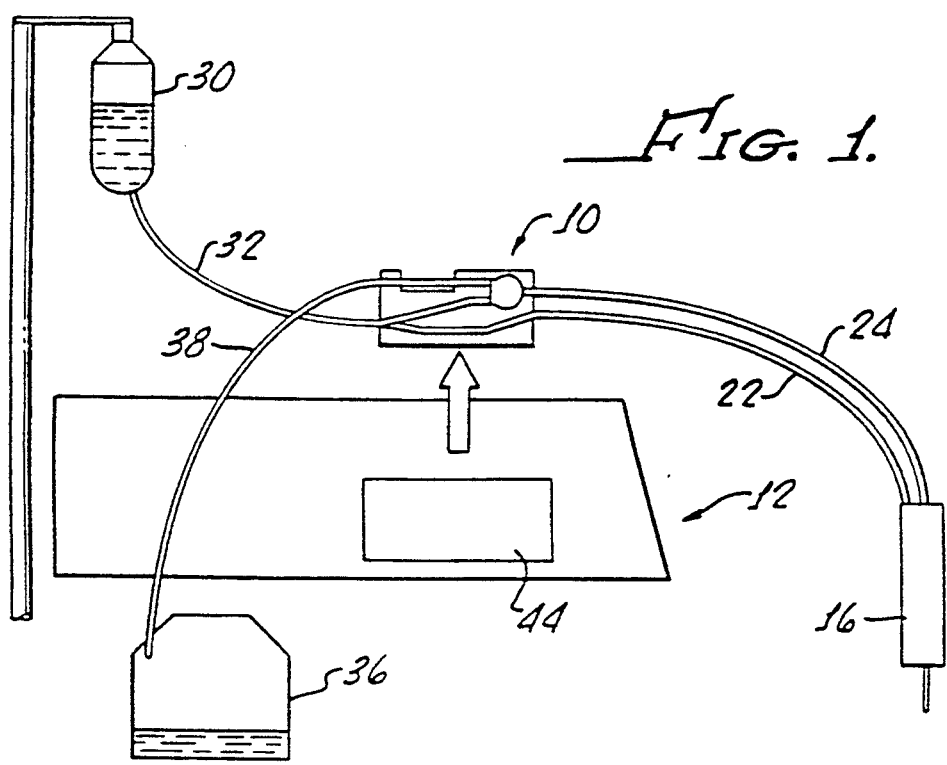
FIG. 1 is a schematic representation of a Phaco system in which the present invention may be used to advantage showing a tubing management system.

In FIG. 1, there is shown a tubing management system (or cassette) 10, in which the present invention may be used to advantage along with an instrument console 12 having a peristaltic pump head 14 (see FIG. 2) and a surgical instrument 16 (see FIG. 1).

Figure 2:
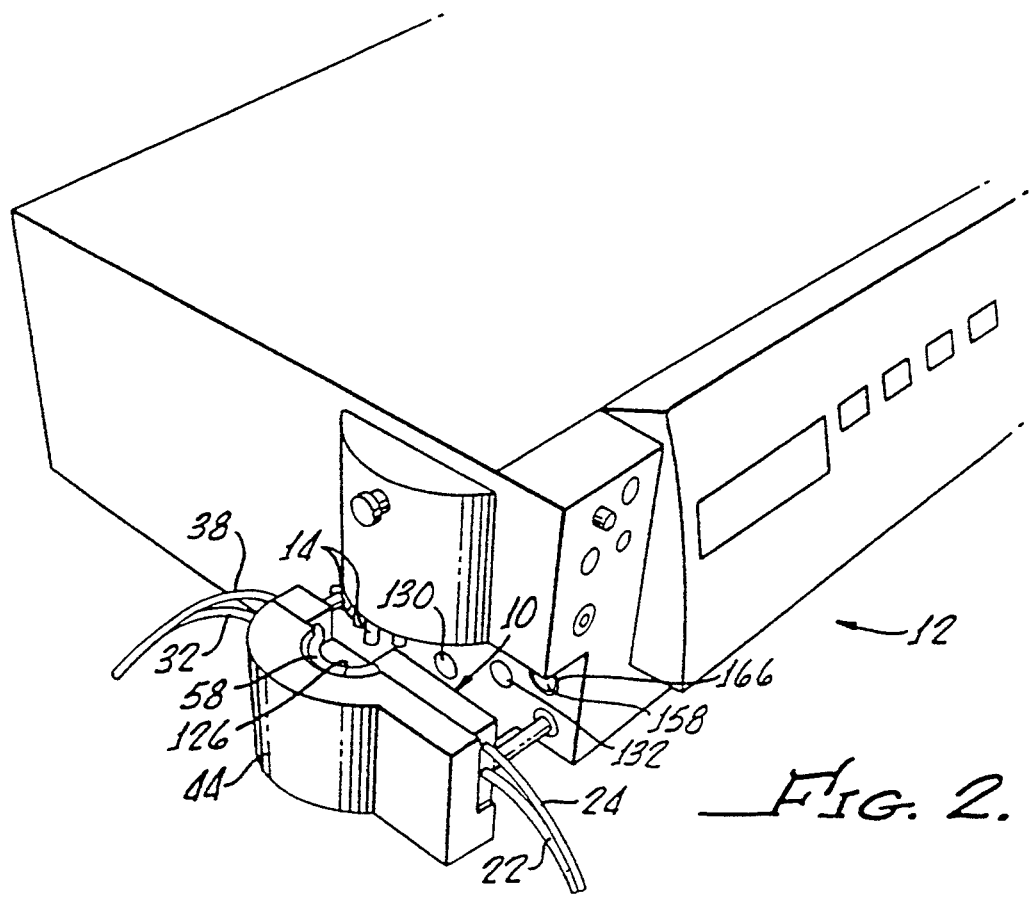
FIG. 2 is a perspective view of the tubing management system as it may be inserted into a console drawer.

As hereinabove described, the present invention is used in conjunction with the surgical instrument or handpiece 16 for ophthalmic surgery, requiring irrigation and aspiration of fluids. As will be hereinafter discussed in greater detail, the cassette 10 is connected with an irrigation line 22 and an aspiration line 24 for providing fluid communication between the surgical handpiece 16 and a source 30 of balanced saline solution (BSS) through a BSS line 32 and also with a waste receptacle 36 through a waste line 38. All these are diagrammatically represented in FIG. 1. As also will be described hereinafter in greater detail, the cassette 10 includes a housing 42 (FIG. 3) which is sized for insertion into a drawer 44 in the console 12 (FIG. 2).

The housing 42 may consist of the rear half 48 and a front half 50 which is formed from any suitable plastic material. If the cassette 10 is disposable, the rear and front halves 48 and 50 may be plastic welded or glued together to form the cassette 10. In this instance, a lower grade of plastic for the cassette 10 may be employed.

Alternatively, if the cassette is to be reused, the rear and front halves 48 and 50 may be snapped or screwed together in any suitable fashion in order to facilitate disassembly of the cassette 10. In this instance, the rear and front halves 48 and 50 should preferably be formed from a plastic suitable for autoclaving.

The rear half 48 includes a channel 50 in order to provide a means for supporting an aspiration tube 58 when the rear half 48 is assembled to the front half to form the housing 42. Openings 62, 64 in the rear half and front half 48 and 50, enable access to the aspiration tube 58 for contact with the peristaltic pump head 14. A manifold 66 includes nipples 68, 70 which provide means for connecting the aspiration tube 58 with the waste line 38.

A pressure transducer measurement system, or diaphragm assembly, 74, in accordance with the present invention, generally includes a housing 76 with an upper inlet 78 which provides a means for connecting the aspiration tube 58 to the aspiration line 24. The diaphragm assembly 74 will be described in greater particularity hereinafter.

The manifold 66 may be formed from a suitable plastic and include a slot 80 for enabling attachment of the manifold 66 to a rib 82 molded into the rear half 48 of the housing 42. A Y formed into the manifold 66 includes an external nipple 88 communicating with nipples 92, 94 which provides means for connecting the irrigation line 32 to both the aspiration line 24 and the irrigation line 22 of the surgical device 16.

An upper transfer tube 100 interconnects the nipple 92 with a lower inlet 102 in the diaphragm housing while a lower transfer tube 104 connected with the lower nipple 94 is connected by nipples 108, 110 to the irrigation line 22 of the surgical instrument 116.

The upper transfer tube 100 is centered in the opening 114 in the front half 50 and the lower transfer tube 104 is centered in opening 116 in the front half and the openings 114, 116 provide a means for enabling the regulation of irrigation fluid flow in the irrigation line 32 into both the irrigation line 22 and aspiration line 24 of the surgical instrument 16.

Bridges 120, 122 formed in the rear half 48 and spanning the openings 114, 116 respectively provide a means for enabling the transfer tubes 100, 104 to be compressed thereagainst, as hereinafter described, in order to regulate the fluid flow in the transfer tubes 100, 104 and thereby divert irrigation fluid from the BSS line 32 into either the irrigation line 22 or aspiration line 24 of the surgical instrument 16.

As hereinabove described, the diversion of irrigation fluid from the line 32 into the aspiration line 24 of the surgical instrument is made in order to free blockages which may occur in the aspiration line 24 from time to time. Importantly, the irrigation of fluid is diverted through the diaphragm housing in order that the pressure thereof during back flushing of the aspiration line 24 may be monitored.

As shown in FIG. 2, the console drawer 44 is sized for accepting the cassette 10 in the manner illustrated with the aspiration tube 58 to a curved portion 126 of the drawer 44 and forced against pump head rollers 14 when the drawer 44 is closed with the cassette 10 therein.

Any conventional peristaltic pump head 14 with rollers 14 may be utilized in conjunction with the curved surface 126 to effect a peristaltic-type pumping of fluid from the aspiration line 24 of the surgical handpiece 16 when the pump head is rotated. The pump head and curved surface may be as described in U.S. Pat. No. 5,230,614, entitled "Reduced Pulsation Tapered Ramp Pump Head". This referenced patent is incorporated into the present application, in toto, by this specific reference thereto.

Also included in the console are solenoid-activated plungers 130, 132 which, when activated, move outwardly from the console to engagement with the transfer tubes 100, 104 respectively through the holes 114,116, in order to compress the transfer tubes 100, 104 against the bridges 120, 122, respectively, in order to divert irrigation fluid from the irrigation line 32 to the diaphragm housing 76 or directly into the irrigation line 22 of the surgical handpiece 16.

The plungers 130, 132 may be activated and operated in any conventional manner through switches in the console 12 or by remote control, as may be desired.

As illustrated in FIG. 4, the pressure transducers measurement system 74 generally includes a cap 140, which is ultrasonically welded to the rear half 48 in an opening 142 therein. The diaphragm 144 is disposed over an opening 146 in the front of the housing 76 and secured and sealed therein by the retainer 150 which is ultrasonically sealed to the housing 76. A ferromagnetic disk 154 is bonded to the diaphragm 144 and provides means for removably coupling the diaphragm to a transducer 158 (see FIG. 2) disposed in the instrument console 12 when the cassette 10 is inserted into the instrument console drawer 44.

The force measurement provided by the system 74 eliminates a number of practical problems associated with the changing characteristics of the diaphragm as a function of its position. A permanent magnet attached to the transducer couples with the ferromagnetic disk 154 when the cassette 10 is disposed in the drawer 44 and closed so that the magnet 166 is abutted with the disk 154 to effect the coupling therebetween (see FIG. 2). Simultaneous with the closing of the drawer, plungers 130, 132 are positioned in a spaced-apart relationship with the transfer tubes 100, 104 in order that engagement therewith may be effected by the movement, or displacement, of the plungers so as to selectively engage and compress the transfer tubes 100, 104 against the bridges 120, 122 respectively.

The diaphragm housing 76 may be coupled to the irrigation line 22 by means of the nipple 170 and therefore enables irrigation fluid diverted through the transfer tube 100 by sealing of the transfer tube 104 against the bridge 122, into the aspiration line 24. Alternatively, when the transfer tube 100 is compressed against the bridge 120, irrigation fluid flows into the irrigation line 24 through the transfer tube 104.

When irrigation fluid is diverted into the aspiration line 24, the peristaltic pump head may be stopped to prevent aspiration of the irrigation fluid directly from the diaphragm housing 76.

During both normal flow of irrigation fluid through the transfer tube 104 and during the back flush of fluids through the transfer tube 100 into the aspiration line 24, it is important that the diaphragm assembly 74 be operative for enabling pressure measurement on a continuous basis in order to monitor the pressure.

Figure 5:
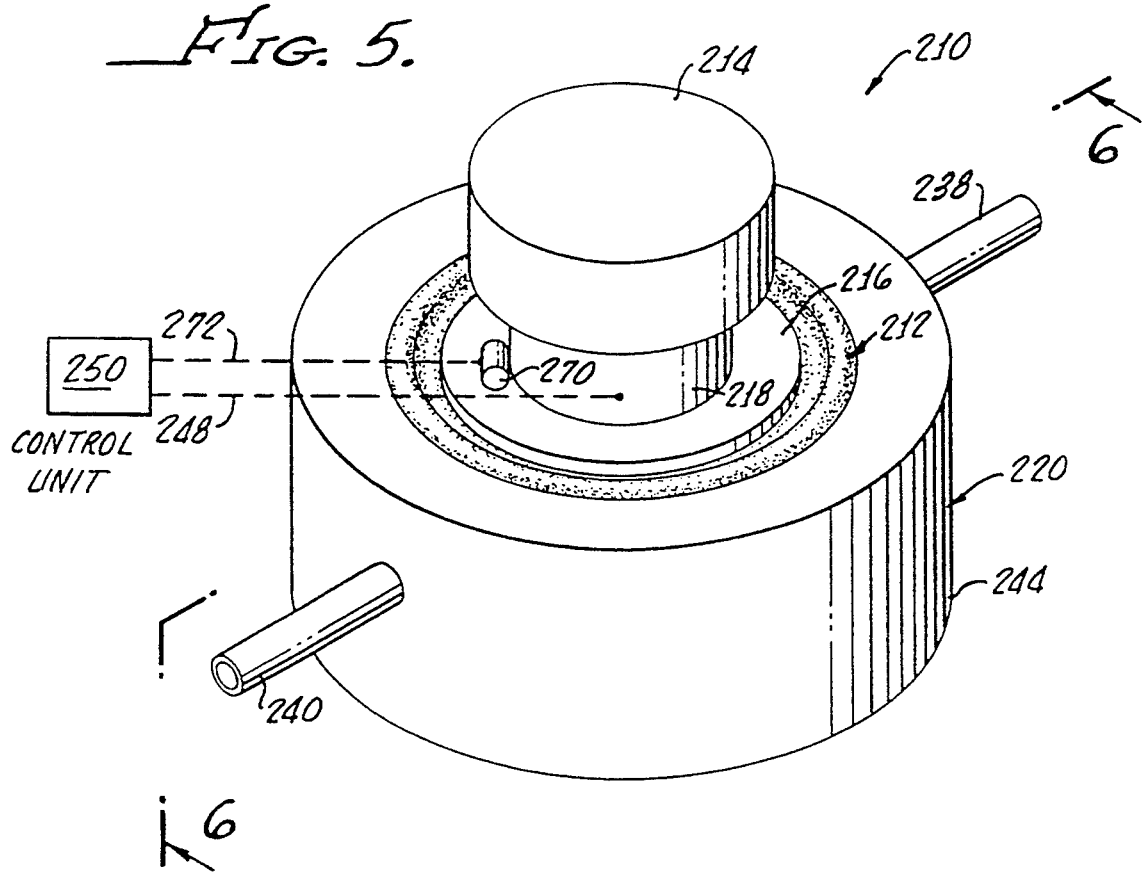
FIG. 5 is a perspective view of an alternative embodiment of the pressure measurement system in accordance with the present invention showing a chamber, diaphragm, force transducer and magnet system for coupling the force transducer to the diaphragm.
Figure 6:
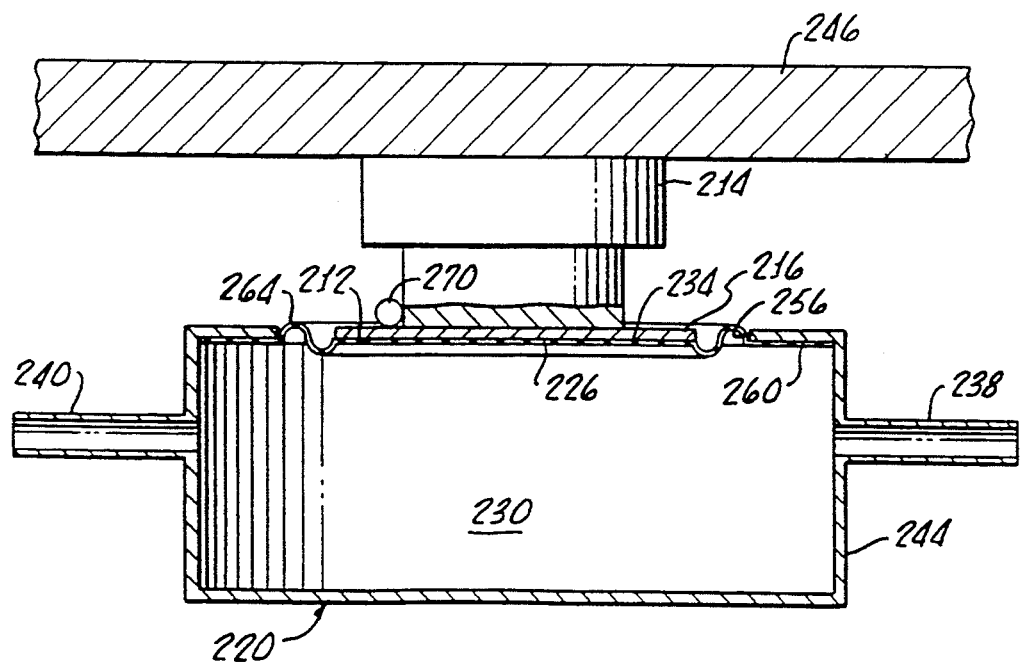
FIG. 6 is a cross-sectional view of the pressure measurement system shown in FIG. 5 taken along the Section 5—5.

Turning now to FIGS. 5 and 6, there is shown an alternative pressure transducer measurement system 210, in accordance with the present invention, generally showing a diaphragm 212, a force transducer 214, a ferromagnetic plate 216, a magnet 218, and a chamber 220.

The chamber 220, which may be formed from any suitable material, may have a diameter of about 1¼ inches and provides a means for exposing one side 226 of the diaphragm 212 to a fluid disposed in an inside 230 of the chamber 220.

As hereinafter described in greater detail, the ferromagnetic plate 216 and magnet 218 provide a means for removably coupling the force transducer 214 to an opposite side 234 of the diaphragm 212.

In providing a means for exposing the one side 226 diaphragm to the fluid, the chamber 220 includes a fluid inlet 238 and a fluid outlet 240 disposed in opposing positions in a curved portion 244 of the chamber 220. The magnet 218 is permanently attached to the transducer 214 and may be of any suitable type, either electromagnetic or permanently magnetic. The transducer 214 is attached to a surface 246 disposed within the console 12.

If an electromagnet is used, suitable coupling by means of wire 248 to a control unit 250 may be utilized for interrupting the current flow to the electromagnet, thus decreasing, or eliminating, the magnetic coupling to the plate 216 for enabling separation of the magnet 218 and transducer 214 from the plate 216.

After removal of the magnet 218 and the transducer 214 from the plate 216, the chamber 220 and diaphragm may be autoclaved or otherwise sterilized without affecting the transducer 214 and permanent magnet 218. After sterilization, the transducer 214 and magnet 218 may be recoupled to the plate 216 as shown in FIGS. 5 and 6. Alternatively, in a disposable system, a replacement chamber (not shown) identical to the chamber 220 shown in the figures may be coupled to the transducer 214 via the permanent magnet 218 as described. Thereupon, selection of the permanent magnet and the coupling force between the magnet 218 and the plate 216, a ferromagnetic substance, may be determined by easy experimentation and, of course, will vary with the dimensions of the diaphragm, plate and transducer 214 requirements.

As shown, the diaphragm 212 is disposed across a circular opening 256 and sealed thereto along an inside surface 260 of the chamber 12. This attachment may be by adhesive or any other bonding system which provides a leak-tight engagement between the surface 260 and the diaphragm 212.

Similarly, the opposite side 234 of the diaphragm 212 is permanently attached to the plate 216 by means of adhesive or any suitable means for bonding of the plate 216 to the diaphragm 212 in a manner enabling autoclaving of the diaphragm 212 without separation. Such bonding techniques are well known in the art.

While the diaphragm 212 may be formed from any suitable material, it is expected that it would be formed from a thin silicon material, for example, about 13 mils thick. In order to enable free movement of the diaphragm in response to the pressure of the fluid within the chamber 220, a circular pleated portion 264 may be formed in the diaphragm 212, with the pleated portion having a diameter greater than the diameter of the plate 216.

Because the transducer 214 responds only to the force exerted by the diaphragm thereon, through the magnet 218, the exact position of the diaphragm 212 with respect to the opening 256 and remaining chamber interior 230 is not important in the operation of the device. This is a significant improvement over prior art devices which are based on displacement of a diaphragm to measure pressure.

While not necessary for the operation of the present system 210, a magnetic detector 270 may be installed in a position sensitive to the presence of the plate 216. This detector 270 may be of any suitable type and may be operated by sensing the magnetic flux of the magnet 218. When the magnet is properly coupled to the plate 216, the magnetic flux exterior to the magnet 218 and plate 216 is significantly less than when the magnet 218 and the plate 216 are separated.

This provides a means for determining proper coupling. The detector 270 may be interconnected by wires 272 to the control system 250 for this purpose. The control system 250 may be any appropriate state-of-the-art electronic circuit suitable for interconnection with the magnetic detector 270 and either indicating a noncoupled configuration and/or providing a signal for interrupting fluid flow into the chamber 220 when a coupling is not proper.

Thus, the system 210, in accordance with the present invention, provides a method of measuring pressure through the use of a force transducer 214 which basically allows the diaphragm 212 to remain substantially stationary. That is, there are no position measurement requirements necessary as in prior art systems. In addition, the nonsterile side of the diaphragm 212 is free from pneumatic or hydraulic contact with many prior art systems involving a secondary closed pneumatic or hydraulic system.

Further, the force transducer 214, which may be a strain gauge, such as, for example, Model MTX220A manufactured by Motorola, is not subject to mechanical overload and inherently remains stable for long periods of time.

With proper selection of a diaphragm and transducer, the system can measure pressures both greater or less than atmospheric pressure, and saturation will not occur if the force transducer 214 is sealed.

Because the diaphragm is uniformly supported and sealed across the opening 256, when no pressure is present in the chamber 220, the resilient nature of the silicon diaphragm 212 will automatically center within the opening which eliminates any long term drift or permanent offset of the diaphragm.

Although there has been hereinabove described a specific pressure measurement system in accordance with the present invention, for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A pressure measurement system comprising:
    a diaphragm;
    means for exposing one side of said diaphragm to a fluid;
    force transducer means for measuring force exerted by said fluid on said one side of said diaphragm with minimal movement of diaphragm position; and
    means for removably coupling said force transducer means to an opposite side of said diaphragm, the means for removably coupling comprising a ferromagnetic plate attached to said diaphragm and magnet means, attached to said force transducer means, for removably engaging the ferromagnetic plate.

2. The system according to claim 1 wherein said means for exposing one side of said diaphragm to a fluid comprises a chamber having a fluid inlet and a fluid outlet and said diaphragm is sealably disposed across an opening in said chamber.

3. The system according to claim 2 wherein said magnet means comprises an electromagnet.

4. The system according to claim 2 wherein said magnet comprises a permanent magnet.

5. The system according to claim 4 wherein said chamber has a cylindrical shape and said opening is disposed in a flat end of the chamber.

6. The system according to claim 5 wherein said opening, diaphragm and plate are circular.

7. The system according to claim 6 wherein said fluid inlet and outlet are disposed in a curved portion of said chamber.

8. The system according to claim 7 further comprising means for detecting magnetic coupling between the magnet and the plate.

9. A fluid pressure measurement system comprising:
    a chamber having a fluid inlet and a fluid outlet, said chamber further including means for defining an opening therein;
    a diaphragm sealably disposed across said opening;
    force transducer means for measuring force exerted on said diaphragm by the fluid in the chamber; and
    means for removably coupling said force transducer means to said diaphragm, the means for removably coupling comprising a ferromagnetic plate attached to said diaphragm and magnet means, attached to said force transducer means, for removably engaging the ferromagnetic plate.

10. The system according to claim 9 wherein said magnet means comprises an electromagnet.

11. The system according to claim 9 wherein said magnet comprises a permanent magnet.

12. The system according to claim 11 wherein said chamber has a cylindrical shape and said opening is disposed in a flat end of the chamber.

13. The system according to claim 12 wherein said opening, diaphragm and plate are circular.

14. The system according to claim 13 wherein said fluid inlet and outlet are disposed in a curved portion of said chamber.

15. The system according to claim 14 further comprising means for detecting magnetic coupling between the magnet and the plate.

* * * * *